(12) United States Patent
Wang (10) Patent No.: US 9,439,999 B2
(45) Date of Patent: Sep. 13, 2016

(54) COMPOSITE COLLAGEN SPONGE AND PREPARATION METHOD THEREOF

(75) Inventor: Shanshan Wang, Harbin (CN)

(73) Assignee: Harbin Peiqilong Biopharmaceutical Co., Ltd (CN)

( * ) Notice: Subject to any disclaimer, the term of this patent is extended or adjusted under 35 U.S.C. 154(b) by 166 days.

(21) Appl. No.: 14/235,355

(22) PCT Filed: Jun. 7, 2012

(86) PCT No.: PCT/CN2012/076577
§ 371 (c)(1),
(2), (4) Date: May 12, 2014

(87) PCT Pub. No.: WO2013/013537
PCT Pub. Date: Jan. 31, 2013

(65) Prior Publication Data
US 2014/0235539 A1    Aug. 21, 2014

(30) Foreign Application Priority Data
Jul. 28, 2011    (CN) .......................... 2011 1 0212713

(51) Int. Cl.
A61L 15/32 (2006.01)
A61L 27/56 (2006.01)
A61L 27/24 (2006.01)
A61K 38/39 (2006.01)
A61L 24/00 (2006.01)
A61L 24/10 (2006.01)
A61K 38/00 (2006.01)

(52) U.S. Cl.
CPC ........ *A61L 24/0036* (2013.01); *A61L 24/0015* (2013.01); *A61L 24/102* (2013.01); *A61L 2300/414* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 4,066,083 A | 1/1978 | Ries | |
| 5,001,169 A | 3/1991 | Nathan et al. | |
| 5,496,559 A * | 3/1996 | Fujioka | A61F 13/02 424/435 |
| 6,180,606 B1 | 1/2001 | Chen et al. | |
| 7,754,258 B2 | 7/2010 | Morgan et al. | |
| 2006/0236891 A1 | 10/2006 | Morgan et al. | |
| 2008/0268052 A1 | 10/2008 | Voytik-Harbin et al. | |
| 2009/0312524 A1 * | 12/2009 | Lauritzen | A61K 38/17 530/356 |

FOREIGN PATENT DOCUMENTS

| | | |
|---|---|---|
| CN | 1228339 A | 9/1999 |
| CN | 1276733 A | 12/2000 |
| CN | 1408411 A | 4/2003 |
| CN | 1486748 A | 4/2004 |
| CN | 14879647 A | 4/2004 |
| CN | 1511592 A | 7/2004 |
| CN | 1915437 A | 2/2007 |
| CN | 101001649 A | 7/2007 |
| CN | 101279104 A | 10/2008 |
| CN | 101612113 A | 12/2009 |
| CN | 102357259 A | 2/2012 |
| DE | 4404625 C1 | 4/1995 |
| DE | 102007037056 A1 | 1/2009 |
| EP | 1356829 A2 | 10/1996 |
| JP | H01-303152 A | 12/1989 |
| JP | 2001-139599 A | 5/2001 |
| JP | 2001-508301 A | 6/2001 |
| JP | 2001-508689 A | 7/2001 |
| JP | 2009540936 A | 11/2009 |
| WO | 9013320 A1 | 11/1990 |
| WO | 9830225 | 7/1998 |
| WO | 9831403 | 8/1998 |
| WO | 9915209 | 4/1999 |
| WO | 0137861 A1 | 5/2001 |
| WO | WO 02/070594 A2 | 9/2002 |
| WO | 2004007707 A1 | 1/2004 |
| WO | 2006005340 | 1/2006 |
| WO | 2008105971 | 8/2008 |
| WO | 2009122902 A1 | 10/2009 |
| WO | 2010062049 A2 | 6/2010 |

OTHER PUBLICATIONS

Kim et al. (2005) Preparation of porcine small intestinal submucosa sponge and their application as a wound dressing in full-thickness skin defect of rat, Internat. J. Biol. Macromol., vol. 36, pp. 54-56.*
Millington-sanders et al. (1998) Structure of chordae tendineae in the left ventricle of the human heart, J. Anat., vol. 192, pp. 573-581.*
Grant et al. (2009) Tuning the Elastic Modulus of Hydrated Collagen Fibrils, Biophys. J., vol. 97, pp. 2985-2992.*
First Office Action and Search report issued on May 6, 2013 for Chinese patent application 201110212713.0 (with the English translation).

(Continued)

Primary Examiner — Anand Desai
Assistant Examiner — Samuel Liu
(74) Attorney, Agent, or Firm — Dilworth IP, LLC (57) ABSTRACT

The present invention discloses a composite collagen sponge and the preparation method thereof. The composite collagen sponge comprises collagen, cell growth factors, and a protecting agent, and has a water absorption capacity of more than 52 times. The preparation method includes a cation chromatographic purification step and a two-stage inactivation step consisting of organic solvent/detergent virus inactivation and dry heat virus inactivation. The composite collagen sponge obtained by the method of the present invention not only improves the safety and performance of the product in clinical applications, but also ensures the stability and the bioactivity throughout the effective life of the product.

8 Claims, 1 Drawing Sheet

(56) References Cited

OTHER PUBLICATIONS

Office Action issued on Aug. 4, 2015 for counterpart Russian patent application No. 2014103549 (with the English translation).
First Office Action issued on Mar. 31, 2015 for counterpart Japanese patent application No. 2014-521915.
Second Office Action issued on Sep. 29, 2015 for counterpart Japanese patent application No. 2014-521915.
Dichetlmuller et al., Robustness of solvent/detergent treatment of plasma derivatives:a data collection from Plasma Protein Therapeutics Association member companies, Transfusion, vol. 49, Sep. 2009, pp. 1931-1943.
Dichtelmuller, et al., Improvement of Virus Safety of a S/D-Treated Factor VIII Concentrate by Additional Dry Heat Treatment at 100 degrees C., Biologicals (1996) 24, 125-130.
EESR issued on Apr. 16, 2015 for European patent application No. 12817662.5.
International Search Report for International Application No. PCT/CN2012/076577, State Intellectual Property Office of the P.R. China, China, mailed on Sep. 20, 2012.

* cited by examiner

COMPOSITE COLLAGEN SPONGE AND PREPARATION METHOD THEREOF

TECHNICAL FIELD

The present invention pertains to the field of biomedical materials and relates to a composite collagen sponge and the preparation method thereof. The composite collagen sponge is used to stop bleeding from wound surfaces of human and animal bodies, and to promote cell growth and proliferation as well as tissue repair of vessels and organs.

BACKGROUND

In the medical field, wound repair and post-op body growth and regeneration are correlated pathological and physiological processes, which involve a series of biochemical, physiological, and morphological changes in the body. Thus, defects often appear on skin and organ surfaces when the body is wounded. In the case where cells are unrecoverable, conditions such as infection, festering, or necrosis of transferred flaps and transplanted skin grafts may occur on the body. Generally, in order to lower the possibility of such phenomena, anti-infection treatment methods are often employed in clinical scenarios, for example, by injecting antibiotics or by externally applying traditional Chinese medicine and western medicine, but the survival rate of tissue cells on the wound surface of the body is very low which results in adverse conditions like muscle defects, scar formation, and an extended period of wound healing and even necessitates re-operation.

To solve the technical problem of how to avoid adverse conditions in wounds and lower the re-operation rate, extensive studies and clinical applications in relation to use of the repairing effect of growth factors on body wounds and post-op body tissues have been conducted since 1980s. The concept of body tissue repair has thus developed from the simple healing of body surfaces to the repair process of cells and tissues, which improves or restores the effect of tissue cell survival by using growth factors to manually intervene in the natural healing of wound surfaces.

Collagen, a structural protein constituting the extracellular matrix, is present as white, transparent, non-branched fibrils made up of several types of glycoprotein molecules and has a quaternary structure. The unit of collagen is tropocollagen, the molecule of which is a slim, triple-stranded helical chain having a diameter of 1.5 nm and a length of 300 nm as measured by electron microscopy and having a relative molecular mass of $2.85 \times 10^5$. It has a stable triple-helix spatial structure due to its special amino-acid composition. Collagen is hemostatic, low antigenic, degradable and biocompatible, and is used to make biomedical materials and also to clinically stop bleeding and promote cell growth.

Fibroblast growth factors (FGF) are mitogenic, chemotactic, and regulatory proteins in all cells associated with wound healing, and promote the repair and regeneration of mesoderm- and ectoderm-derived cells (e.g., epithelial cells, hypodermal cells, fibroblasts, and vascular endothelial cells).

US 2006/0236891, US 1978/4,066,083, US 20080268052 and US 2010/7,754,258 disclose methods for preparing collagen membranes by using collagens extracted from Achilles tendons or skin of animals, while none of them mentions measures for virus inactivation. However, in clinical applications, there are always possibilities of cross-infections by pathogenic microorganisms infective to both human and animals, for example, Encephalitis B virus (EBV), Hepatitis E virus (HEV), Pseudorabies virus (PRV), Vesicular stomatitis virus (VSV), and *Streptococcus*, all of which once caused widespread human-animal cross-infective diseases and disastrous results. Therefore, products manufactured by these preparation methods have certain safety risks in clinical applications.

CN 1228339 and CN1511592 disclose composite collagen sponges incorporated with biological factors, but they employed radiation to carry out disinfection during preparation of these sponges. With respect to bioactive materials, radiation will increase the temperature of the products, resulting in denaturation of the bioactive materials, which not only lowers the activity of the bioactive materials but also leads to generation of new immuno-active materials and therefore causes unnecessary troubles in clinical applications.

Moreover, the activity of the product decreases during long-term storage, which may affect its clinical efficacy and effective life. However, in the abovementioned patent documents, no protecting measures were taken and no investigations were performed regarding the stability of the incorporated bioactive materials, and virus inactivation effectiveness was not verified either.

SUMMARY OF THE INVENTION

In order to solve the above technical problems, the present invention proposes a composite collagen sponge and the preparation method thereof. Specifically, the present invention includes the following aspects.

1. The present invention provides a composite collagen sponge comprising collagen and cell growth factors, and having a water absorption capacity of more than 52 times.

2. The composite collagen sponge according to above 1, having an elastic modulus of more than 70.0 N/cm.

3. The composite collagen sponge according to above 2, further comprising a protecting agent at a content of 10% to 50% by weight on the basis of the composite collagen sponge, said protecting agent comprising amino acids, saccharides and albumin in a weight ratio of (1 to 11):(1.25 to 17.5):(1 to 7.5), wherein the amino acids are at least one amino acid selected from leucine, isoleucine, glycine, alanine, and serine; and the saccharides are at least one saccharide selected from glucose, lactose, sucrose, trehalose, and mannitol.

4. The composite collagen sponge according to above 3, wherein the protecting agent is added such that the amino acids added into a collagen solution have a final concentration of 2.0 to 22 mg/ml, preferably 2.5 to 15 mg/ml; the saccharides added into the collagen solution have a final concentration of 2.5 to 35 mg/ml, preferably 3.0 to 15 mg/ml; and the human serum albumin added into the collagen solution has a final concentration of 2 to 15 mg/ml.

5. The composite collagen sponge according to above 4, wherein the protecting agent further comprises glycerol which is added into the collagen solution at a final concentration of 1.0 to 15 mg/ml. Thus, when the composite collagen sponge comprises glycerol, the weight ratio of glycerol to saccharide in the protecting agent is (0.5 to 7.5):(1.25 to 17.5).

6. A composite collagen sponge comprising collagen, cell growth factors, and the protecting agent according to any one of above 3 to 5.

7. The present invention further provides a method for preparing the composite collagen sponge according to any one of above 1 to 6, wherein a step of purifying the collagen includes a purification process using ion exchange chromatography which is a preparative chromatography with CM52 cation exchange resin, and the eluents are pH 4.5 solutions containing sodium chloride at concentrations from 0.2 mol/L to 0.8 mol/L and sodium acetate at a concentration of 0.1 mol/L.

8. The method for preparing the composite collagen sponge according to above 7, wherein a virus inactivation step includes a two-stage virus inactivation process:
the first stage of virus inactivation is virus inactivation with an organic solvent/detergent;
the second stage of virus inactivation is a 30 to 120 minute-treatment of the composite collagen sponge solution in a water bath at 90 to 100° C.

9. The method for preparing the composite collagen sponge according to above 8, wherein the organic solvent/detergent is a mixture of polysorbate 80 and tributyl phosphate, and the polysorbate 80 and the tributyl phosphate are added into the collagen solution in such amounts that the final concentration of polysorbate 80 is 1% and the final concentration of tributyl phosphate is 0.3%; preferably, under the condition where the collagen concentration is controlled at 30 to 70 mg/mL and the pH is controlled at 6.0 to 8.0, a mixed sterile aqueous solution containing polysorbate 80 and tributyl phosphate is slowly added into the collagen solution until the final concentration of polysorbate 80 is 1% and the final concentration of tributyl phosphate is 0.3%, and virus inactivation is performed at 24 to 26° C. for 6 to 8 hours.

10. The method for preparing the composite collagen sponge according to any one of above 6 to 9, wherein the second stage of virus inactivation is carried out in the presence of a protecting agent which is added into the collagen solution in such an amount that the final concentration of the amino acids constituting the protecting agent is 2.0 to 22 mg/ml, the final concentration of the saccharides is 2.5 to 35 mg/ml and the final solution of the albumin is 2 to 15 mg/ml; preferably, the protecting agent further comprises glycerol such that the final concentration of the glycerol added in the collagen solution is 1.0 to 15 mg/ml.

The composite collagen sponge of the present invention can promote regeneration of capillary vessels, improve local blood circulation, accelerate healing of wound surfaces, and are useful for burn wound surfaces (including superficial second degree, deep second degree, and granulation wound surfaces), chronic wound surfaces (including body surface chronic ulcer etc.) and fresh wound surfaces (including trauma, wound surfaces at skin donor sites, operation wound etc.). The composite collagen sponge product of the present invention can maintain the stability of bioactive materials during long-term storage, have a high water absorption capacity, a high elastic modulus, and excellent flexibility, and may exert superior effects in clinical applications.

BRIEF DESCRIPTION OF THE DRAWINGS

In FIG. 1, a indicates a standard marker of relative molecular masses; b indicates a standard collagen sample; and c indicates a collagen sample of the present invention.

The raw material for the collagen of the present invention may be fresh mammalian connective tissue or skin of pigs. In a particular embodiment of the present invention, the collagen is a type I collagen extracted from skin of pigs, and during its extraction, purification is carried out by salting-out in combination with chromatography to afford a highly pure, non-immunogenic collagen having a substantially improved water absorption capacity and elastic modulus; the collagen obtained from the extraction is subjected to two-stage virus inactivation to lower the risk of contamination of the resultant collagen sponge by pathogenic microorganisms and to reduce the impact on bioactive materials. Further, upon addition of an effective protecting agent, the obtained composite collagen sponge product will be highly stable.

The composite collagen sponge provided by the present invention uses collagen as a matrix within which growth factors, e.g., basic fibroblast growth factor (FGF), are evenly distributed, and the content of FGF per square centimeter of the composite collagen sponge may be 200 U to 1500 U.

The composite collagen sponge prepared by the present invention may be manufactured into a product having a length of 2.5 to 10 cm, a width of 2.5 to 5.0 cm and a thickness of 0.3 to 2.0 cm.

The composite collagen sponge provided by the present invention is also characterized by a collagen purity of more than 99.0%, a water absorption capacity of more than 52 times, and an ash content of less than 1.0%.

The composite collagen sponge provided by the present invention has an elastic modulus of more than 70.0 N/cm and the pores formed therein generally have a diameter of 50 to 100 μm. The sponge can release FGF continuously over a period of 0 to 100 h so as to improve the therapeutic effect on wounds.

In order to lower the risk of bearing viruses in the collagen sponge product and to ensure safety of the product, if e following two-stage virus inactivation process is employed in the method for preparing the collagen sponge of the present invention, in addition to processes for tightening the screening and control of the raw material.

The first stage of S/D virus inactivation process: a virus inactivator (e.g., a solvent/detergent (S/D)) is added into the collagen solution obtained after extraction, so as to inactivate lipid-enveloped viruses. Specifically, under continuous stirring at 50 to 200 rpm, an aqueous solution containing polysorbate 80 and tributyl phosphate is added slowly into the collagen solution and homogenized by stirring until the final concentration of polysorbate 80 is 1% and the final concentration of tributyl phosphate is 0.3%, and then virus inactivation is carried out at 24° C. to 26° C. for 6 to 8 hours.

With the epidemic Encephalitis B virus and the Pseudorabies virus serving as the indicator viruses, the above process results in an inactivation of these indicator viruses of more than 4 logs, which meets the safety requirements.

In the above virus inactivation process, overly high collagen concentrations will affect the result of virus inactivation, and therefore the collagen concentration is generally controlled at 30 to 70 mg/ml and the above S/D virus inactivation process is carried out at pH 6.0 to 8.0.

The second stage of virus inactivation: the product is inactivated at 90° C. to 100° C. for 30 to 120 minutes. For example, the product is packaged with aluminum-plastic material, put into a water-bathed inactivation cabinet, and subjected to a water bath treatment at 90° C. to 100° C. for 30 to 120 minutes. Virus inactivation treatments adopting such a water-bath inactivation process instead of radiation can result in effective inactivation of non-lipid-enveloped DNA and RNA viruses.

During the second stage of virus inactivation, the inactivation condition of 90° C. to 100° C. and 30 to 120 minutes may affect the bioactivities of the collagen and growth factors. To solve this problem, in the second stage of virus inactivation of the present invention, a protecting agent comprising amino acids, saccharides and albumin is added in the collagen solution. In order to make the resultant composite collagen sponge softer and more elastic, an appropriate amount of glycerol may be incorporated into the protecting agent.

The amino acids or salts thereof used in the protecting agent are one or two amino acids or salts thereof selected from leucine, isoleucine, glycine, alanine, and serine. The final concentration of the amino acids or salts thereof added in the collagen solution is generally 2.0 to 22 mg/ml, preferably 2.5 to 15 mg/ml.

The saccharides used in the protecting agent are at least one selected from glucose, lactose, sucrose, trehalose, and mannitol. The final concentration of the saccharides added in the collagen solution is generally 2.5 to 35 mg/ml, preferably 3.0 to 15 mg/ml.

If the protecting agent contains glycerol, the final concentration of glycerol added in the collagen solution is generally 1.0 to 15 mg/ml.

When the product is applied in clinical scenarios, the albumin used in the protecting agent is preferably human serum albumin. The final concentration of human serum albumin added in the collagen solution is generally 2 mg/ml or more, but not more than 15 mg/ml.

The collagen of the present invention is extracted from animal skin. When the product is applied in clinical scenarios, type I collagen extracted from skin of pigs is preferably used. In the formulated composite collagen sponge solution, the content of the collagen is usually 30 mg/ml or more, and the concentration of fibroblast growth factors is usually 400 to 3000 U/ml.

The S/D virus inactivation method is generally suitable for blood preparations. Adding organic solvents/detergents into blood preparations to inactivate lipid-enveloped viruses is a conventional method and the organic solvents/detergents used are polysorbate 80 and tributyl phosphate. However, polysorbate 80 and tributyl phosphate have certain adverse effects, and thus their residual amounts need to be controlled during subsequent purification of collagen such that the residual polysorbate 80 is less than 100 µg/ml and the residual tributyl phosphate is less than 10 µg/ml.

In the present invention, polysorbate 80 and tributyl phosphate can be effectively removed by performing the salting-out twice and performing chromatographic purification so that the residual polysorbate 80 is less than 10 µg/ml and the residual tributyl phosphate is less than 2 µg/ml.

The antigenicity of collagen is primarily attributed to the non-helical regions at the termini of a collagen molecule, i.e., the C-terminal peptide and the N-terminal peptide. In the present invention, the non-helical regions at the termini of the molecule are cleaved off by pepsin, and these terminal peptides are removed through extraction and purification to give a highly pure collagen to be used for preparation of collagen sponges. During purification by salting-out, an aqueous solution of NaCl at a concentration of 2.0 to 3.5 mol/L, preferably 2.0 to 2.5 mol/L, is used, and the temperature is kept at 0° C. to 4° C. for 4 to 12 h. During purification by CM52 cation exchange chromatography, aqueous solutions of NaCl at concentrations from 0.2 to 0.8 mol/L and a pH of 3.5 to 4.5 are used for gradient elution, and preferably aqueous solutions at pH 4.5 each containing 0.1 mol/L sodium acetate and 0.2 mol/L, 0.4 mol/L, or 0.6 mol/L NaCl are used for gradient elution. Upon SDS-PAGE electrophoresis examination, the collagen of the present invention is found to have a complete triple-helical structure and maintains full bioactivity, and the purity of the collagen reaches 96% (W/W) or more, even 99.0% or more, as examined and calculated, which prevents immunogenic reactions caused by the collagens of low purity extracted by traditional purification methods.

For lyophilization of the product, the product is firstly subjected to freezing at −40 to −45° C. for 3 to 5 h, and then vacuum dried with a vacuum degree controlled at no more than 20 Pa; the temperature of the product is raised to 20° C. in 10 to 15 h at a controlled temperature rising rate, and the product is maintained at 20 to 25° C. for 2 to 5 h; and the water content in the lyophilized product is kept at 5% or less to ensure the activity of biological factors.

Specifically, the steps of preparing the composite collagen sponge of the present invention are as follows.

Step 1. Raw Material Selection and Degreasing Treatment

Fresh connective tissue of mammals or skin of pigs having passed quarantine and inspection were taken as raw materials and treated by the following process: the hair and inside fat of the pig skin were removed with a blade; the processed pig skin was weighed and placed in a stainless-steel container, to which an aqueous solution of sodium carbonate was added in a weight ratio of the raw material pig skin to an aqueous solution of 10%-35% (W/W) (preferably 25%) sodium carbonate of 1:(1 to 10) (preferably 1:5) to soak the pig skin for 20 to 60 min (preferably 20 min) while stirring was performed once every 5 minutes; the pig skin was removed out of the container after the soaking, and washed 10 times with pure water; water was drained off, and impurities such as fat or hair follicles in the raw material were scraped off with a stainless steel cutting tool.

Step 2. Grinding Procedure

The pig skin processed in step 1 was weighed, sliced into stripes in a cutting machine, then cut into 0.2 to 0.5 $cm^2$ pieces with a cryogenic grinder, and poured into a stainless-steel container to which a 75% ethanol solution was added to soak the pieces for 20 minutes; and afterwards the pieces were taken out, washed repeatedly for 10 times with pure water, then washed repeatedly for 5 times with cooled water for injection, and drained.

Step 3. Enzymolysis Procedure

Water for injection at 0 to 4° C. was added to the pig skin raw material processed in step 2 in a weight ratio of 1:5 to 30 (for example, a ratio of pig skin to water of 1 kg:10 kg) and thoroughly mixed; the mixture was pumped into a colloid mill by a peristaltic pump in which the cooling circulation system was pre-started to control the temperature at 0° C. to 4° C., and then homogenized; the homogenate liquid was transferred into an enzymolysis tank to which an aqueous solution of 1.0 M acetic acid was slowly added dropwise to adjust the pH to 2.5-3.5, preferably 2.5; pepsin was added (5 to 10 g pepsin per 1 kg of the raw material obtained from step 2), and the enzymolysis temperature was controlled between 10° C. and 20° C.; and enzymolysis was performed for 20 to 24 h, and the enzymatic lysate at this point was a viscous and uniform colloidal fluid.

Step 4. Inactivation Procedure of Pepsin

An aqueous solution of 20% by weight of sodium hydroxide was slowly added into the enzymatic lysate processed in step 3 to adjust the pH to 9.0; the lysate was maintained at 0 to 4° C. for 10 h; and then the pH was adjusted to 6.5 with an aqueous solution of 1.0 M acetic acid.

Step 5. Filtration Procedure

Water for injection was added into the enzymatic lysate processed in step 4 (the enzymatic lysate was diluted in a weight ratio of lysate to water of 1:1 to 10) and mixed thoroughly such that the collagen concentration was 30 to 70 mg/ml, preferably 30 mg/ml; the mixture was roughly filtered through a filter element with a pore size of 40 μm and, then finely filtered through a filter element with a pore size of 1.0 μm to a special tank for virus inactivation.

Step 6. S/D Virus Inactivation Procedure

Under continuous stirring at 50 to 200 rpm, an aqueous solution containing polysorbate 80 and tributyl phosphate was slowly added to the solution processed in step 5, the mixture was stirred till uniformity such that the final concentration of polysorbate 80 was 1% (by weight) and the final concentration of tributyl phosphate was 0.3% (by weight), and virus inactivation was performed at 24 to 26° C. for 6 to 8 h, preferably 6 h.

Step 7. Salting-Out Procedure

NaCl was added to the solution processed in step 6 under stirring with a stirrer at a rotating rate of 100 to 500 rpm such that the final concentration of NaCl was 2.0 to 2.5 mol/L, preferably 2.5 mol/L, and the mixture was maintained at 0 to 4° C. for 4 h. The mixture was centrifuged at 0 to 4° C. in a continuous refrigerated centrifuge at 14,000 to 16,000 rpm for 60 to 30 min, and the supernatant was discarded; the precipitate was taken and added to an aqueous solution of 0.3 M acetic acid in a weight ratio of precipitate to 0.3 M acetic acid solution=1:10 to 15, and then stirred till the precipitate was completely dissolved; NaCl was added to a final concentration of NaCl of 2.05 to 2.5 mol/L, preferably 2.5 mol/L; and then the mixture was centrifuged to afford collagen precipitate.

Step 8. Desalting Procedure

A cold solution of 95% ethanol was added to the collagen precipitate obtained in step 7 in a weight ratio of the collagen precipitate to the cold 95% ethanol=1:3 to 8, and stirred till uniformity; the mixture was centrifuged at 0 to 4° C., 8000 rpm for 30 min, the supernatant was discarded and the precipitate was collected; and the above process was repeated once. A 0.1 mol/L sodium acetate solution at pH 4.5 was added to the collagen precipitate in a weight ratio of the collagen precipitate:the sodium acetate solution=1:8 to 20, and stirred till uniformity; and the mixture was filtered through a filter having a filter element with a pore size of 0.45 μm, and transferred to the CM cation chromatographic purification procedure.

Step 9: CM52 Cation Exchange Chromatographic Purification Procedure

A preparative chromatographic column packed with CM52 cation exchange resin (10×100 cm) was equilibrated with 10 bed volumes of 0.1 mol/L sodium acetate buffer at pH 4.5, and the sample was then loaded at a loading rate of 20.0 to 30.0 ml/min, preferably 23.0 ml/min; the column was eluted with 5 bed volumes of 0.1 mol/L sodium acetate aqueous solution at pH 4.5 containing 0.2 mol/L NaCl, and then with a 0.1 mol/L sodium acetate aqueous solution at pH 4.5 containing 0.4 mol/L NaCl, the protein eluate was collected when its peak started to appear, and then the column was eluted with 5 bed volumes of 0.1 mol/L sodium acetate aqueous solution at pH 4.5 containing 0.6 mol/L NaCl, wherein the detection wavelength was 215 nm.

Step 10. Ultra-Filtration Procedure

The collected collagen eluate was ultra-filtered through a Tangential Flow ultra-filter (Millipore) having a cut-off value of 10 kD and a membrane area of 4 m$^2$ to undergo concentration and desalting, in which the eluate was firstly concentrated to ⅓ of the initial volume and supplemented with ⅔ of water for injection to the initial volume, then again concentrated to ⅓ of the initial volume and supplemented with ⅔ of water for injection to the initial volume, and then concentrated to ⅓ of the initial volume; during the concentration, the pressure at the inlet of the ultra-filter was less than 0.15 MPa throughout concentration; and the trapped solution of collagen was collected.

Step 11. Formulation Procedure

The concentration of the collagen solution obtained in step 10 was adjusted to 40 to 70 mg/ml, and a 1000 ml solution of composite collagen sponge was prepared according to the formulation shown in Table 1.

Step 12. Sterilization Procedure by Filtration

The formulated solution was filtered consecutively with filters equipped with polyethersulfone filter elements having a pore size of 0.45 μm and a pore size of 0.22 lam (PALL).

Step 13. Lyophilization Procedure

The solution treated in step 12 was added into a 15 cm×5 cm stainless steel mould and the dispensed liquid was 37 ml, the mould was then placed into a lyophilizer for lyophilization, and the water in the solution was removed by a cryogenic lyophilization method, in which the solution was firstly frozen at −40° C. for 4 h and then vacuum dried with the vacuum degree controlled at not more than 20 Pa, the temperature of the product was increased to 20° C. in 15 h at a controlled temperature elevating rate and was maintained at 25° C. for 4 h.

Step 14. Second-Stage Virus Inactivation Procedure

The lyophilized product was packaged with aluminum-plastic material in an aluminum-plastic material packaging machine, and then placed into a water-bathed sterile cabinet to carry out water-bath virus inactivation. After the virus inactivation was completed, the product was stored at 2 to 8° C. away from light before use.

EXAMPLE 1-3

The above steps of preparing the composite collagen sponge were followed under the conditions listed in Table 1 below, and samples 1-3 were obtained.

TABLE 1

|  |  | Example 1 | Example 2 | Example 3 |
|---|---|---|---|---|
| Step 1 | Skin of pigs (kg) | 0.5 | 1.5 | 2.5 |
|  | Concentration of the sodium carbonate solution (wt %) | 10% | 25% | 30% |
|  | Weight ratio of pig skin to sodium carbonate solution | 1:1 | 1:5 | 1:10 |
|  | Duration (min) | 20 | 40 | 60 |

TABLE 1-continued

|  |  | Example 1 | Example 2 | Example 3 |
|---|---|---|---|---|
| Step 3 | Weight ratio of pig skin to water for injection | 1:5 | 1:10 | 1:30 |
|  | target pH adjusted with acetic acid | 2.5 | 3.0 | 3.5 |
|  | Amount of pepsin added | 1:0.005 | 1:0.008 | 1:0.01 |
|  | Temperature for enzymolysis (° C.) | 10 | 15 | 20 |
|  | Duration of enzymolysis (h) | 24 | 22 | 20 |
| Step 5 | Weight ratio of enzymatic lysate to water for injection | 1:10 | 1:5 | 1:1 |
|  | Collagen concentration | 40 | 45 | 60 |
| Step 6 | Adding 11% polysorbate 80 to a final concentration of | 1% | 1% | 1% |
|  | Adding a 3.3% tributyl phosphate aqueous solution to a final concentration of | 0.3% | 0.3% | 0.3% |
|  | Temperature for virus inactivation (° C.) | 24 | 25 | 26 |
|  | Duration of virus inactivation (h) | 6 | 7 | 8 |
| Step 7 | Adding NaCl to a final concentration of | 2.0 | 2.0 | 2.5 |
|  | Centrifugation Speed | 14000 | 15000 | 16000 |
|  | Duration of centrifugation | 60 | 50 | 30 |
|  | Weight ratio of precipitate to 0.3M acetic acid aqueous solution | 1:10 | 1:12 | 1:15 |
| Step 8 | Weight ratio of collagen precipitate to 95% ethanol | 1:3 | 1:5 | 1:8 |
|  | Weight ratio of collagen precipitate to 0.1 mol/L sodium acetate solution | 1:8 | 1:10 | 1:20 |
| Step 9 | Loading rate (ml/min) | 20.0 | 23.0 | 30.0 |
|  | Concentrations of NaCl solutions for gradient elution | 0.2, 0.4, 0.6 | 0.2, 0.4, 0.6 | 0.2, 0.4, 0.6 |
|  | pH of NaCl solutions for gradient elution | 4.5 | 4.5 | 4.5 |
| Step 11 | Amount of each component added to prepare a 1000 ml solution |  |  |  |
|  | Collagen (mg) | 40,000 | 50,000 | 70,000 |
|  | Fibroblast factor (U) | 3,000,000 | 1,000,000 | 400,000 |
|  | Glycerol (mg) | 1,500 | 10,000 | 15,000 |
|  | Saccharide(s) (mg) | 3,000 | 10,000 | 15,000 |
|  | Amino acid(s) (mg) | 2,500 | 10,000 | 15,000 |
|  | 20% w/v human serum albumin (ml) | 10 | 40 | 75 |
| Step 14 | Temperature (° C.) | 100 | 95 | 90 |
|  | Time (min) | 30 | 60 | 120 |
| Sample obtained |  | Sample 1 | Sample 2 | Sample 3 |
| Collagen purity (%) |  | 99.0 | 99.4 | 99.6 |
| Water absorption capacity (×times) |  | 55 | 60 | 58 |
| Elastic modulus (N/cm) |  | 75 | 80 | 78 |

In the protecting agent of Example 1, glycine was used as the amino acid, and sucrose was used as the saccharide; in the protecting agent of Example 2, leucine and isoleucine in a weight ratio of 1:1 were used as the amino acids, and glucose and trehalose in a weight ratio of 1:2 were used as the saccharides; and in the protecting agent of Example 3, alanine and serine in a weight ratio of 1:1 were used as the amino acids, and lactose and mannitol in a weight ratio of 1:2 were used as the saccharides.

5. Examination Results (1) Verification of the Effectiveness of S/D Virus Inactivation The effectiveness of S/D virus inactivation was verified. Epidemic Encephalitis B virus and Pseudorabies virus were used as indicator viruses; the cells cultured were BHK21 cells; and the calculation is carried out with the 96-well microplate cytopathic effect method and according to the Karber method. The results are shown in Tables 2 and 3.

Tables 2 and 3

TABLE 2

Results of the S/D inactivation of Epidemic Encephalitis B virus in enzymatic lysates

| | Residual Epidemic Encephalitis B virus titer ($LgTCID_{50}/0.1$ ml) | | |
|---|---|---|---|
| | Example 1 | Example 2 | Example 3 |
| Control samples | 6.063 | 6.313 | 6.063 |
| Treated samples | 0.500 | 0.500 | 0.500 |
| Reduction of the virus | 5.563 | 5.813 | 5.563 |

Results:
Reduction of the virus in Example 1 ≥5.563 $LgTCID_{50}/0.1$ ml
Reduction of the virus in Example 2 ≥5.813 $LgTCID_{50}/0.1$ ml
Reduction of the virus in Example 3 ≥5.563 $LgTCID_{50}/0.1$ ml

TABLE 3

Results of the S/D inactivation of Pseudorabies virus in enzymatic lysates

| | Residual Pseudorabies virus titer (LgTCID$_{50}$/0.1 ml) | | |
|---|---|---|---|
| | Example 1 | Example 2 | Example 3 |
| Control samples | 5.563 | 5.313 | 4.875 |
| Treated samples | 0.500 | 0.500 | 0.500 |
| Reduction of the virus | 5.063 | 4.813 | 4.375 |

Results:
Example 1 ≥5.063 LgTCID$_{50}$/0.1 ml
Example 2 ≥4.813 LgTCID$_{50}$/0.1 ml
Example 3 ≥4.375 LgTCID$_{50}$/0.1 ml The results of the verification demonstrate an inactivation of indicator viruses of more than 4 logs after a S/D treatment of the collagen solution, which meets the safety requirements. That is, it is effective to perform virus inactivation at 24 to 26° C. for 6 to 8 h, with polysorbate 80 at a final concentration of 1% and tributyl phosphate at a final concentration of 0.3% under the condition where the collagen concentration is controlled at 30 to 70 mg/ml and pH is 6.5 to 7.5.

(2) After water-bath virus inactivation, samples were taken to verify the effectiveness of the inactivation. Epidemic Encephalitis B virus, Pseudorabies virus, and Porcine parvovirus were used as indicator viruses; the cells cultured were BHK21 cells; and the calculation is carried out with the 96-well microplate cytopathic effect method and according to the Karber method. The results are shown in Tables 4, 5, and 6.

TABLE 4

Results of the water-bath inactivation of Epidemic Encephalitis B virus

| | Residual Epidemic Encephalitis B virus titer (LgTCID$_{50}$/0.1 ml) | | |
|---|---|---|---|
| | Example 1 | Example 2 | Example 3 |
| Control samples | 5.438 | 5.688 | 5.563 |
| Treated samples | 0.500 | 0.500 | 0.500 |
| Reduction of the virus | 4.938 | 5.188 | 5.063 |

Results:
Example 1 ≥4.938 LgTCID$_{50}$/0.1 ml
Example 2 ≥5.188 LgTCID$_{50}$/0.1 ml
Example 3 ≥5.063 LgTCID$_{50}$/0.1 ml

TABLE 5

Results of the water-bath inactivation of Pseudorabies virus

| | Residual Pseudorabies virus titer (LgTCID$_{50}$/0.1 ml) | | |
|---|---|---|---|
| | Example 1 | Example 2 | Example 3 |
| Control samples | 5.063 | 5.563 | 5.688 |
| Treated samples | 0.500 | 0.500 | 0.500 |
| Reduction of the virus | 4.563 | 5.063 | 5.188 |

Results:
Example 1 ≥4.563 LgTCID$_{50}$/0.1 ml
Example 2 ≥5.063 LgTCID$_{50}$/0.1 ml
Example 3 ≥5.188 LgTCID$_{50}$/0.1 ml

TABLE 6

Results of the water-bath inactivation of Porcine parvovirus

| | Residual Porcine parvovirus titer (LgTCID$_{50}$/0.1 ml) | | |
|---|---|---|---|
| | Example 1 | Example 2 | Example 3 |
| Control samples | 5.313 | 5.250 | 5.625 |
| Treated samples | 0.500 | 0.500 | 0.500 |
| Reduction of the virus | 4.813 | 4.750 | 5.125 |

Results:
Example 1 ≥4.813 LgTCID$_{50}$/0.1 ml
Example 2 ≥4.750 LgTCID$_{50}$/0.1 ml
Example 3 ≥5.125 LgTCID$_{50}$/0.1 ml The results of the verification demonstrate an inactivation of indicator viruses of more than 4 logs after water-bath inactivation of the samples, which meets the safety requirements.

(3) Examination of Collagen Purity

Figure 1:
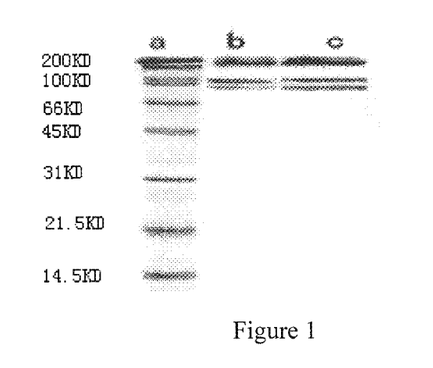
FIG. 1 is an electrophoresis photograph for the collagen of the present invention.

After chromatographic purification, collagen samples were taken for collagen purity examination. Control samples of collagen of the same mass concentration were prepared. Chromatographically purified samples and non-chromatographically purified samples were mixed with the sample-treating solution and heated for 5 min in a boiling water bath, then subjected to electrophoresis on a gel of a 5% concentrating gel and a 10% separating gel, stained with Coomassie Brilliant Blue 8250, and destained in 7.5% acetic acid and 5% methanol. The loading volume was 10 μl. Type I collagen control sample was purchased from Sigma. Electrophoresis analysis illustrated that the collagen treated by chromatographic purification showed the same bands as those of the control sample and was a typical type I collagen, and no other impurity bands were observed, indicating that the extracted sample was highly pure. Electrophoresis images are shown in FIG. 1. In FIG. 1, a indicates a standard marker of relative molecular masses; b indicates a standard collagen sample; and c indicates the collagen sample obtained in Example 2 of the present invention.

(4) Measurement of Collagen Content

Total proteins were determined by the Kjeldahl method, and the content of hydroxyl proline in the hydrolysate was measured by the Woessener method. The collagen content was calculated according to the formula $M_1=M_0/14\%$ and then compared to the total protein to calculate the purity of the collagen. The content of collagen in Example 2 of the present invention is not less than that of the control, suggesting very high purity. The results are shown in Table 7.

TABLE 7

Results of the measurement of collagen content

| | Before chromatographic purification | After chromatographic purification | Control sample |
|---|---|---|---|
| Collagen | 91.5% (m/m) | 99.4% (m/m) | 99.0% (m/m) |

(5) Residual Amounts of Polysorbate 80 and Tributyl Phosphate

After chromatographic purification, samples were taken for measuring the residual amounts of polysorbate 80 and tributyl phosphate, in order to confirm the removal effectiveness.

Based on the fact that the blue complex formed by the reaction of the polyoxyethylene in polysorbate 80 with ammonium cobalt thiocyanate is soluble in dichloromethane, polysorbate 80 was measured by colorimetry at 620 nm. The polysorbate 80 control sample is CAS Registry Number: 9005-65-6 (US Pharmacopeia (USP) standard). The residual amount of tributyl phosphate in the sample to be tested was measured by gas chromatography. The tributyl phosphate control sample is CAS Registry Number: 126-73-8 (Europe Pharmacopeia (EP) standard). Chromatography instrument: Shimadzu GC-14C with a capillary column of acid-modified polyethylene glycol and a flame ionization detector; loading volume: 0.1 μl. The results demonstrated that the amounts of residual polysorbate 80 and tributyl phosphate in the product after chromatographic purification were very low, which meets the safety requirements. The detection results are shown in Table 8.

TABLE 8

Detection results for residual polysorbate 80 and tributyl phosphate after chromatographic purification

| Composition | polysorbate 80 (μg/ml) | Tributyl phosphate (μg/ml) |
|---|---|---|
| Example 1 | 5 | Not Detected |
| Example 2 | 6 | Not Detected |
| Example 3 | 3 | Not Detected | that the amounts of FGF added were different, and samples 7 and 8 were subjected to a long-term-stability investigation together with sample 4. The results show that addition of amino acids, albumin, saccharides and glycerol as a protecting agent to the formulation can effectively ensure the bioactivity of the product throughout its effective life.

TABLE 9

Composition of the composite collagen sponge

| Composition | Sample 4 | Sample 5 | Sample 6 |
|---|---|---|---|
| Collagen | 35.0 mg/ml | 30.0 mg/ml | 32.0 mg/ml |
| FGF | 3000 U/ml | 3000 U/ml | 3000 U/ml |
| Glycerol | 1.5 mg/ml | 1.5 mg/ml | 1.5 mg/ml |
| Sucrose | 3.0 mg/ml | 3.0 mg/ml | 3.0 mg/ml |
| Glycine | 2.5 mg/ml | 2.5 mg/ml | — |
| Human serum albumin | 2.0 mg/ml | — | — |

TABLE 10

Examination results for FGF activity

| | Sample 4 | | Sample 5 | | Sample 6 | |
|---|---|---|---|---|---|---|
| | Before Inactivation | After Inactivation | Before Inactivation | After Inactivation | Before Inactivation | After Inactivation |
| Co60 Radiation 10 kG | 1500 U/cm$^2$ | 1200 U/cm$^2$ | 1450 U/cm$^2$ | 1250 U/cm$^2$ | 1500 U/cm$^2$ | 1280 U/cm$^2$ |
| 100° C., 30 min | 1500 U/cm$^2$ | 1460 U/cm$^2$ | 1450 U/cm$^2$ | 1380 U/cm$^2$ | 1500 U/cm$^2$ | 1390 U/cm$^2$ |

(6) Difference Between FGF Activities Before and After the Water-Bath Inactivation Samples 4, 5, and 6 were prepared by the same method as that in Example 1 except that the composition of the composite collagen sponge shown in Table 9 was used.

Fibroblast growth factor (FGF) was measured with the NIH3T3 cells by the cell proliferation method/MTT colorimetry. FGF is stimulative to the growth of NIH3T3 cells, and the growth state of the NIH3T3 cells varies depending on the FGF bioactivity, which is utilized to measure the activity of FGF. An FGF standard sample was purchased from the Institute of Medicines and Biological Products Identification of China, and NIH3T3 cells were purchased from the Cell Library of Typical Culture Committee of the Chinese Academy of Sciences. The measurement results are shown in Tables 10 and 11.

The measurement results show that a 10 kG Co60 radiation is considerably detrimental to the activity of FGF. When the 10 kG Co60 radiation is compared with the condition of 100° C./30 min, the data show P<0.01 after processed with the SPSS software, which means they can be compared.

Samples 7 and 8 were obtained by preparing collagen sponges by the same method as that in Example 1, except

TABLE 11

Examination results for the long-term stability of FGF

| Composition | 1 month | 6 months | 12 months | 24 months | yield % |
|---|---|---|---|---|---|
| Sample 4 | 1500 U/cm$^2$ | 1450/cm$^2$ | 1420/cm$^2$ | 1390/cm$^2$ | 92.67 |
| Sample 7 | 1480 U/cm$^2$ | 1420 U/cm$^2$ | 1380 U/cm$^2$ | 1360 U/cm$^2$ | 91.89 |
| Sample 8 | 1420 U/cm$^2$ | 1400 U/cm$^2$ | 1350 U/cm$^2$ | 1300 U/cm$^2$ | 91.54 |

(7) Comparison of Water Absorption Capacities

Water absorption capacities of Samples 1, 2 and 3 obtained in Examples 1, 2 and 3 were examined and compared with that of a control sample. A piece of sponge was taken and precisely weighed (precise to 0.1 mg), immersed into pure water at 20° C., and gently kneaded without causing any rupture; when it was fully soaked with water, the sponge was taken out of water by gently nipping a corner with small forceps, and hung above the water surface for 2 minutes before weighing. The mass was compared with the mass of the collagen sponge. The results of the examination and comparison are shown in FIG. 2.

Figure 2:
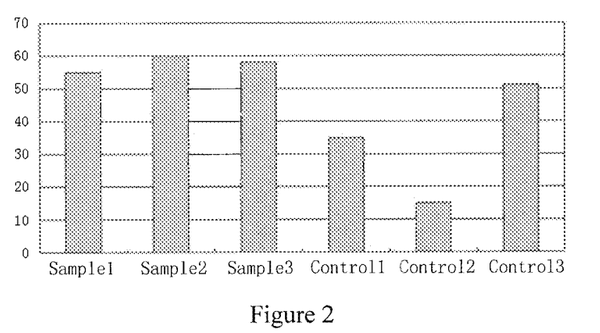
FIG. 2 shows a comparison between the water absorption capacity of a sample of the present invention and that of a control sample.

In FIG. 2, the Y axis represents water absorption (mass/mass); Control 1 is a water absorption standard for a absorptive gelatin sponge in the "US Pharmacopoeia" (USP32-NF27); Control 2 is a collagen sponge prepared according to Example 1 of the Chinese Patent CN 101279104; Control 3 is a collagen sponge prepared according to the Examples of the Chinese Patent CN 1915437. As shown in FIG. 2, the composite collagen sponges of the present invention all have a water absorption capacity of 52 times or more, whereas the collagen sponges prepared according to the prior art or the existing collagen sponge all have a water absorption capacity lower than that of the present invention.

(8) Comparison of Elastic Modulus

Figure 3:
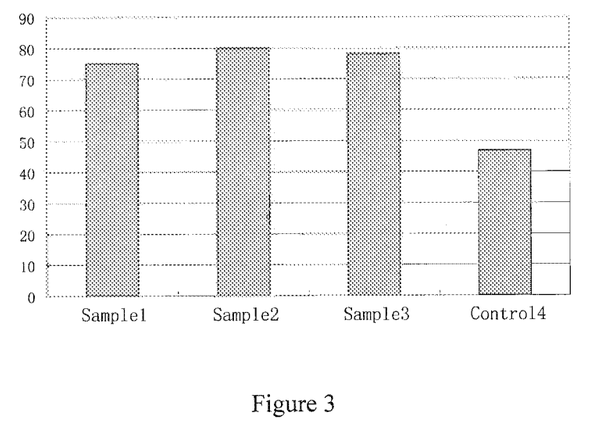
FIG. 3 shows a comparison between the elastic modulus of a sample of the present invention and that of a control sample.

A sample was fixed at both ends on the jigs of a tension tester, and the instrument was started to separate and pull the sample at a certain speed, and the change in the stress on the sample was measured until the sample was broken. The results of the examination and comparison are shown in FIG. 3. In FIG. 3, the Y axis is the elastic modulus (N/cm); Control 4 is a collagen sponge prepared by the methods disclosed in CN 1487967A. It is shown in FIG. 3 that the samples of the present invention have an elastic modulus of more than 70.0 N/cm, whereas the elastic modulus of the collagen sponge prepared according to the prior art is less than 50.0 N/cm.

What is claimed is:

1. A composite collagen sponge comprising collagen, at least one cell growth factor, and a protecting agent comprising at least one amino acid, at least one saccharide, and human serum albumin in a weight ratio of 1.25:1.5:1 for the amino acid, saccharide, and albumin, the composite collagen sponge having a water absorption capacity of more than 52 times the weight of the composite collagen sponge, having an elastic modulus of more than 70.0 N/cm$^2$, wherein the at least one amino acid is selected from the group consisting of leucine, isoleucine, glycine, alanine, serine, and a combination thereof, and the at least one saccharide is selected from the group consisting of glucose, lactose, sucrose, trehalose, mannitol, and a combination thereof.

2. The composite collagen sponge according to claim 1, wherein the protecting agent further comprises glycerol.

3. The composite collagen sponge according to claim 1, wherein the at least one growth factor is a fibroblast growth factor.

4. The composite collagen sponge according to claim 1, wherein the composite is a lyophilized composite.

5. The composite collagen sponge according to claim 1 wherein the collagen is more than 99.0% pure based on the dry weight of the collagen.

6. The composite collagen sponge according to claim 1 wherein the collagen is more than 99.0% pure as determined by SDS-PAGE electrophoresis.

7. The composite collagen sponge according to claim 1 wherein the collagen is more than 99.0% pure and up to about 100% pure based on the dry weight of the collagen.

8. The composite collagen sponge according to claim 1 wherein the collagen is more than 99.0% pure and up to about 100% pure as determined by SDS-PAGE electrophoresis.

* * * * *